(12) United States Patent
Jaccard

(10) Patent No.: US 8,388,563 B2
(45) Date of Patent: Mar. 5, 2013

(54) SPLINT, PARTICULARLY FOR THE WRIST, AND PRODUCTION METHOD THEREFOR

(75) Inventor: Jean-Patrick Jaccard, Caslano (CH)

(73) Assignee: Sports & Supports Limited, Dublin (IE)

( * ) Notice: Subject to any disclaimer, the term of this patent is extended or adjusted under 35 U.S.C. 154(b) by 553 days.

(21) Appl. No.: 12/526,679

(22) PCT Filed: Nov. 27, 2007

(86) PCT No.: PCT/EP2007/010284
§ 371 (c)(1),
(2), (4) Date: Aug. 11, 2009

(87) PCT Pub. No.: WO2008/104205
PCT Pub. Date: Sep. 4, 2008

(65) Prior Publication Data
US 2010/0010407 A1    Jan. 14, 2010

(30) Foreign Application Priority Data

Feb. 27, 2007   (IT) .............................. MI2007A0378

(51) Int. Cl.
*A61F 5/00* (2006.01)
*A61F 5/37* (2006.01)
(52) U.S. Cl. ............... 602/5; 602/21; 128/878; 128/879
(58) Field of Classification Search ............... 602/5, 12, 602/20–27; 2/22, 24; 128/878–879; 36/50.1, 36/51; 24/306, 712.1, 712, 712.2
See application file for complete search history.

(56) References Cited

U.S. PATENT DOCUMENTS

| 2,266,083 | A | * | 12/1941 | Bruno ........................ 24/712.4 |
| 6,893,410 | B1 | | 5/2005 | Hely |
| 7,874,997 | B2 | * | 1/2011 | Jaccard ........................ 602/27 |
| 2008/0287848 | A1 | * | 11/2008 | Jaccard ........................ 602/21 |

FOREIGN PATENT DOCUMENTS

| EP | 0 820 741 | | 1/1998 |
| WO | 2006/032325 | | 3/2006 |
| WO | WO 2006032325 A1 | * | 3/2006 |
| WO | 2006/117808 | | 11/2006 |

OTHER PUBLICATIONS

International Search Report dated Feb. 6, 2008, from corresponding PCT application.

* cited by examiner

*Primary Examiner* — Patricia Bianco
*Assistant Examiner* — Ophelia A Hawthorne
(74) *Attorney, Agent, or Firm* — Young & Thompson

(57) ABSTRACT

A splint, in particular for the wrist, includes a substantially rectangular main band adapted to be closed in a tubular shape around the part of the body to be protected, a plurality of laces having an end integral with one side of the main band, at least one gripping element joined to the other end of the laces and adapted to be fastened on the upper surface of the main band. The splint further includes a comb-shaped insert, provided with teeth spaced apart from each other so as to form gaps wherein the laces can be inserted. A fastening strip is connected to the teeth of the insert and is adapted to be fastened on the upper surface of the main band.

19 Claims, 3 Drawing Sheets

SPLINT, PARTICULARLY FOR THE WRIST, AND PRODUCTION METHOD THEREFOR

BACKGROUND OF THE INVENTION

1. Field of the Invention

The present invention refers to the field of items for healthcare and orthopaedic use for the rehabilitation and the prevention of injuries. It refers in particular to a splint (or brace) for the wrist and to a production method therefor.

2. Description of the Related Art

Various types of splints are known on the market, which comprise a main band, which is closed in a ring, in a tubular shape, around the part of the body to be protected.

To allow the adjustment of the closure and the tightening of the splint, some types of splint have laces, which are joined to the main band. A fastening strip, which can be coupled to the main band, is mounted slidably on the laces. At the ends of the laces gripping elements, which can be coupled to the main band, are provided.

The adjustment of the splint on the user's limb takes place as follows:
- first, the main band is wrapped in a ring around the part of the body to be protected;
- then, the slidable fastening strip is pulled, adjusted in position and fastened on the solid band; and
- lastly, the gripping elements of the laces are pulled to tighten the laces and fastened on the main band.

The procedure for producing such a splint entails the following steps:
- initially the main band with the laces is made;
- the free ends of the laces are inserted into the respective holes in the fastening strip; and
- subsequently the ends of the laces are gathered together in groups and joined to the respective gripping elements.

It is obvious that the stage of inserting the laces into the holes of the fastening strip is somewhat complex, long and costly. In fact this stage is generally carried out manually, by inserting the laces one at a time into the holes of the fastening strip. The application of the gripping elements to the ends of the laces is also complex.

SUMMARY OF THE INVENTION

An object of the present invention is to overcome the drawbacks of the prior art, by providing a splint that is comfortable, versatile, adjustable and at the same time cheap and simple to make.

Another object of the present invention is to provide such a method for manufacturing a splint that is cheap, practical and easy to carry out.

Advantageous embodiments of invention are apparent from the dependent claims.

The splint according to the invention comprises:
- a substantially rectangular main band, adapted to be closed in a tubular shape around the part of the body to be protected,
- a plurality of laces having one end integral with one side of said main band,
- at least one gripping element joined to the other end of said laces and adapted to be fastened on the upper surface of the main band.

The gripping element can be gripped by the user to tighten the laces and to close the main band in a tubular configuration around the part of the body to be protected.

The splint further comprises:
- a comb-shaped insert, provided with teeth spaced apart from each other so as to form gaps within which the laces can be inserted, and
- a fastening strip connected to said teeth of the insert and adapted to be fastened on the upper surface of the main band.

The comb-shaped insert can be applied to the laces simply, rapidly and automatically, avoiding the operations of manual insertion of the laces into holes in the fastening strip.

BRIEF DESCRIPTION OF THE DRAWING FIGURES

Further characteristics of the invention will be made clearer by the detailed description that follows, referring to a purely exemplifying and therefore non limiting embodiment thereof, illustrated in the appended drawing, wherein.

DETAILED DESCRIPTION OF THE INVENTION

Figure 1:
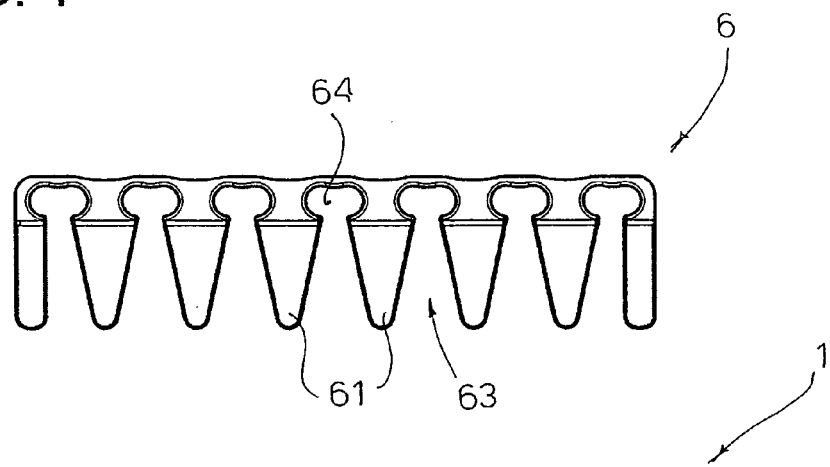
FIG. 1 is a plan view illustrating a main band from the side destined to face towards the user's skin and, exploded, an insert of a splint-closing strip according to the invention.
Figure 1:
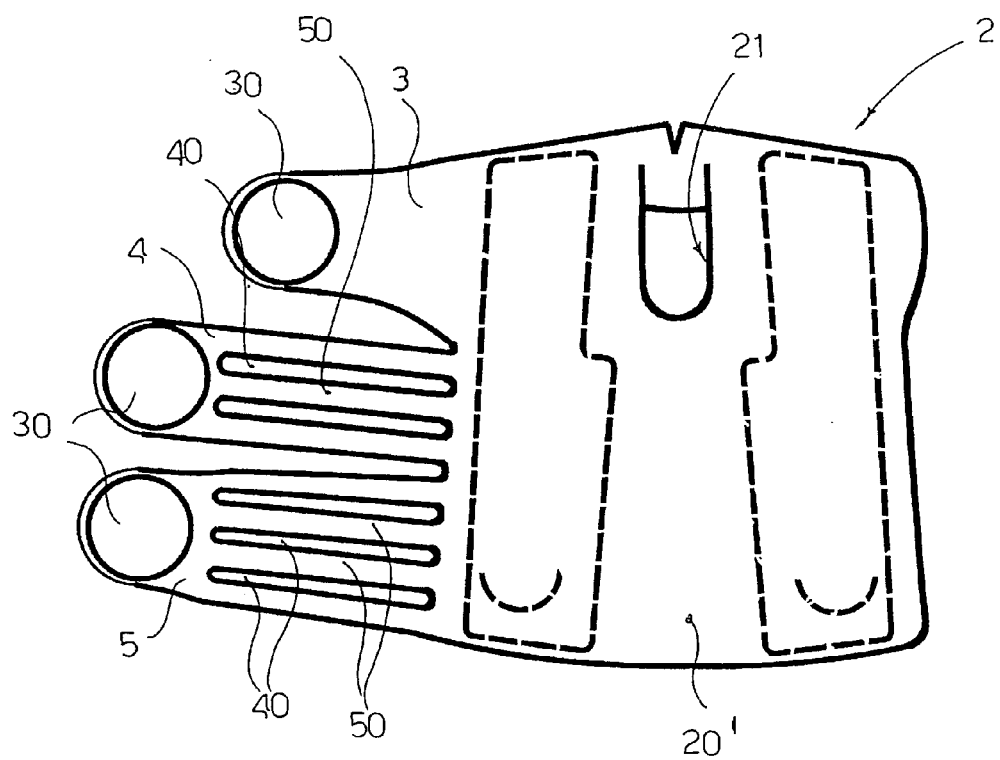

The splint according to the invention, denoted as a whole with the reference numeral 1, is described with the aid of the figures. Even if a wrist splint (wrist support) is shown in the figures, the invention can also extend to other types of splints, such as knee supports, ankle supports, corsets and the like.

The splint 1 comprises a main band 2, substantially rectangular in shape, adapted to be closed in a ring, so as to form a tube surrounding the part of the patient's body to be protected. The main band 2 is obtained from a multi-ply sheet consisting of a plurality of layers of material coupled to each other preferably by flame coupling. Said multi-ply sheet comprises:
- a bottom layer 20' (FIG. 1) of non-allergenic material destined to come into contact with the user's skin,
- an intermediate padding layer of shock-absorbing and breathable material such as, for example, an open cell foamed plastic material, such as polyurethane (PU), and
- a top layer 20 (FIG. 3), destined to face outwards, made of Nylon fabric suitably treated so as to form a surface adapted for a Velcro-type coupling.

The main band 2 thus has an upper surface 20 with a plurality of loops adapted to couple, in a fastening relationship, with a plurality of matching hooks of a Velcro-type fastening element, as will be described hereunder.

Three side straps (3, 4, 5) protrude transversally from one side of the main band.

The first side strap 3 is shorter than the other two side straps 4 and 5.

As shown in FIG. 1, respective gripping elements 30, in the form of a circular tab, are placed at the ends of each side strap (3, 4, 5), on the surface destined to face towards the user's skin. The gripping elements 30 can be applied to the end of the side straps 3, 4 and 5 by sewing or by gluing. Each gripping element 30 has an outer surface with a plurality of Velcro-type fastening elements (hooks) adapted to engage with matching fastening elements (loops) on the upper surface 20 of the main band 2.

Long slits 40 are formed in the second and in the third side strap (4, 5) by die cutting or by slicing, so as to define laces 50, which extend to the gripping element 30. By way of example, as shown in the drawings, two slits 40 are formed in the second side strap 4 so as to form three laces 50 and three slits 40 are formed in the third side strap 5 so as to form four laces 50.

A slit 21 of such a size as to allow the thumb of a hand to be inserted is formed by die cutting in the middle portion of the main band 2, to the front and level with the side strap 3. The slit 21 extends lengthwise along the main band 2.

Figure 3:
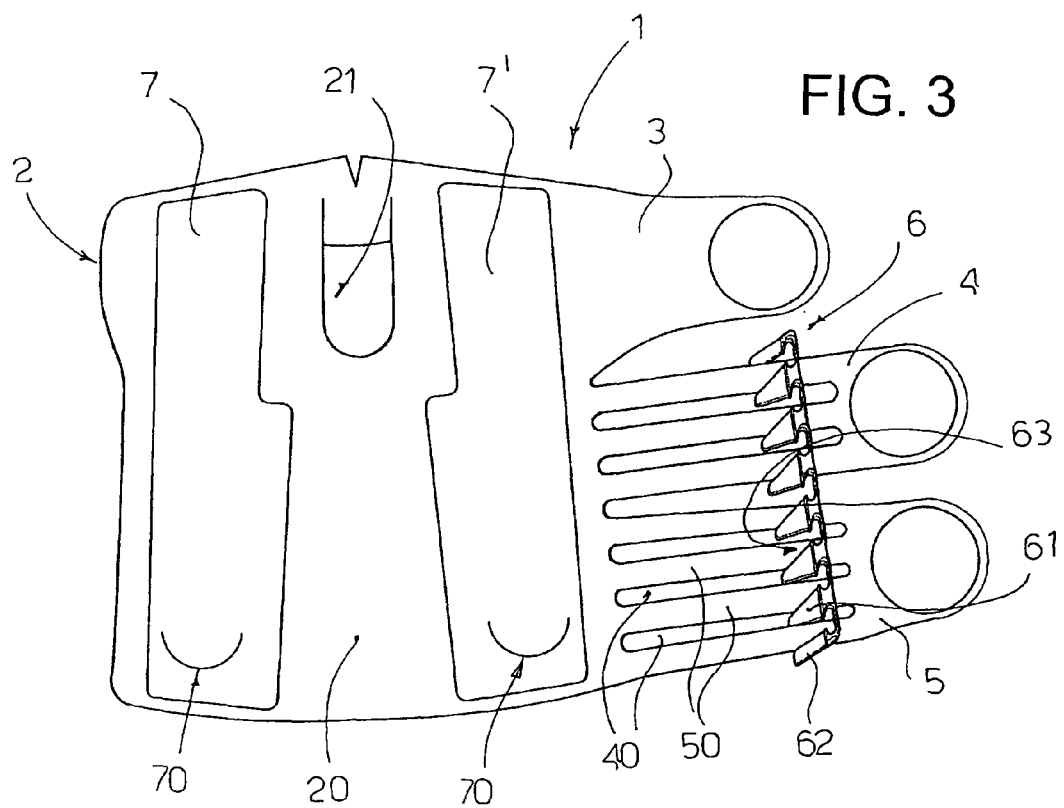
FIG. 3 is a plan view showing the main band from the outward facing side, in which the insert is coupled to the laces of the main band of the splint according to the invention.

As shown in FIG. 3, two longitudinal pockets 7 and 7', which extend substantially for the whole length of the main band 2, are applied by sewing to the upper surface 20 of the main band 2, on one side and on the other with respect to the slit 21. The pockets 7 and 7' have in their rear end respective openings 70 for insertion of metal plates to stiffen the structure.

The palmar stiffening plate destined to be positioned beneath the palm of the hand is inserted into the pocket 7' proximal to the laces 50. The palmar plate has a curved portion of smaller width destined to be disposed level with the first side strap 3.

The dorsal stiffening plate destined to be positioned on the back of the hand is inserted into the pocket 7 distal to the laces 50. The dorsal plate is flat and straight.

The pockets 7 and 7' are made of a material having a Velcro-type outer surface (plurality of loops) like the upper surface 20 of the main band, adapted to be engaged by the gripping elements 30.

Figure 2:
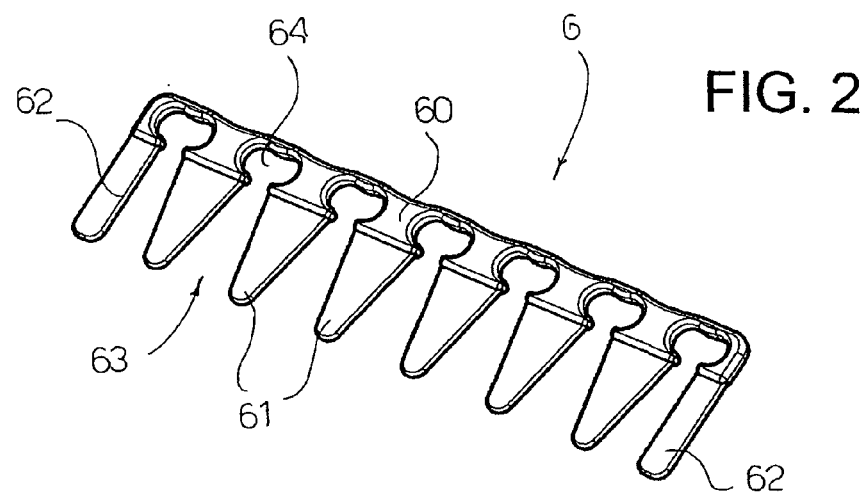
FIG. 2 is a perspective view of the insert of FIG. 1.

As shown better in FIG. 2, the splint according to the invention comprises an insert 6 which is substantially comb-shaped. The insert 6 comprises a base plate 60 from which a plurality of teeth (61, 62) extends. The two end teeth 62 are substantially rectangular, whereas the intermediate teeth 61 are tapered in the shape of an isosceles triangle. In this manner triangular gaps 63, which end in respective C-shaped seats 64 formed in the base plate 60, are formed between the teeth 61 of the insert.

The insert 6 is made by injection moulding of plastic material, such as, for example, polyamide (Nylon).

As shown in FIG. 3, the insert 6 is applied to the side straps 4 and 5. That is to say, the teeth 61 of the insert are inserted into the slits 40 in the side straps, whereas the laces 50 of the side straps can slide in the gaps 63 in the insert.

Figure 4:
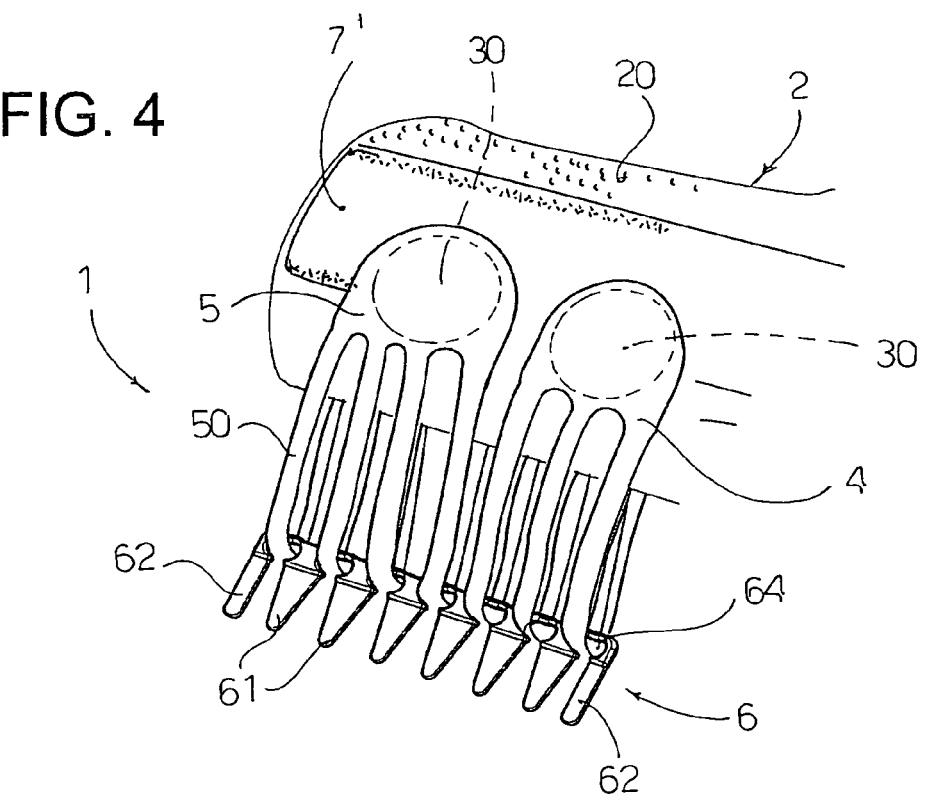
FIG. 4 is a perspective view showing the main band of FIG. 3 closed in a tubular shape.
Figure 5:
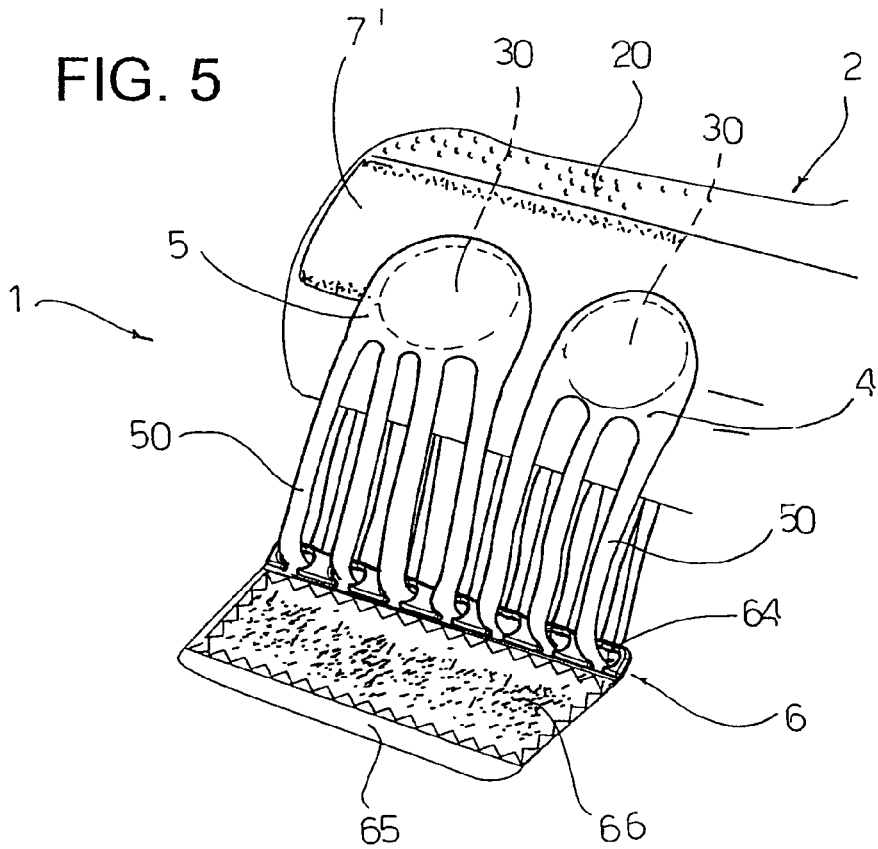
FIG. 5 is a perspective view, like FIG. 4, in which a closing strip joined to the insert is shown.

As shown in FIG. 4, the gripping elements 30 of the side straps 4 and 5 are secured to the upper surface 20 of the main band and the insert 6 is pulled so that the laces 50 engage, in a snap coupling relationship, in the C-shaped seats 64 of the insert (FIG. 4). It should be noted that the width of the C-shaped seats 64 is slightly greater than the width of the laces 50; in this manner the laces 50 are free to slide in the seats 64 of the insert.

In this situation the teeth 61 and 62 of the insert protrude outwards. At this point a fastening strip 65 is applied to the teeth of the insert. The fastening strip 65 can be secured to the teeth of the insert 6 by sewing, so as to surround all the teeth 61 and 62.

The fastening strip 65 has an outer surface 66 provided with Velcro-type fastening elements (hooks) adapted to engage with the fastening elements (loops) on the upper surface 20 of the main band 2. The insert 6 can slide on the laces 5, 5'[50; N.d.T.] so as to be able to adjust the position of the fastening strip 65.

The production method of such a splint proves extremely simple and rapid.

In fact the starting point is a multi-ply sheet obtained by flame coupling of three layers. The multi-ply sheet is die cut so as to obtain the main band 2, the side straps 3, 4 and 5, the slits 40 defining the laces 50 and the central slit 21. The gripping elements 30, the pockets 7 and 7' and the insert 6 are applied to the die-cut sheet, inserting the teeth 61 of the insert into the slits 40 between the laces. Lastly, the fastening strip 65 is secured on the teeth 61 and 62 of the insert.

This procedure can be completely automated and does not require manual operations.

The finished splint 1 is slipped over the user's wrist so that the thumb of the hand enters the slit 21 in the splint. The user then takes the fastening strip 65 with the other hand and fastens it to the upper surface 20 of the main band 2, substantially level with the pocket 7', so as to surround the wrist with the main band 2 and the laces 50.

Subsequently the user grips the end of the third side strap 5 so as to tighten the four laces 50 as much as possible and then blocks the gripping element 30 of the third side strap 5 on the upper surface 20 of the main band 2 level with the pocket 7; then he grips the end of the second side strap 4 so as to tighten the group of three laces 50 as much as possible and then blocks the gripping element 30 of the second side strap 4 on the upper surface 20 of the main band 2.

Lastly the user grips the end of the first side strap 3, so as to tighten it as much as possible and then blocks the gripping element 30 of the first side strap 3 on the upper surface 20 of the main band 2.

It should be noted that during the application of the splint 1, the bottom surface of the laces 50 can come into contact with the user's skin. This is not a problem since the bottom surface of the laces is made of the same non-allergenic material as the bottom surface 20' of the main band 2.

Numerous changes and modifications of detail within the reach of a person skilled in the art can be made to the present embodiment of the invention without thereby departing from the scope of the invention as set forth in the appended claims.

The invention claimed is:

1. A splint comprising:
   a substantially rectangular main band, adapted to be closed in a tubular shape around a part of a body to be protected;
   a plurality of slits die cut to form a plurality of laces each having a first end integrally joined to the splint with the first end integrally joined with one side of said substantially rectangular main band;
   at least one gripping element connected to a second end of said laces and adapted to be fastened to an upper surface of the substantially rectangular main band, said at least one gripping element being able to be gripped by a user to tighten the laces and to close said substantially rectangular main band in a tubular configuration around the part of the body to be protected;
   a comb-shaped insert provided with teeth spaced apart from each other so as to form gaps wherein said laces can be inserted, said teeth having a tapered shape or an isosceles triangle shape; and
   a fastening strip joined to said teeth of the comb-shaped insert and adapted to be fastened onto the upper surface of the substantially rectangular main band.

2. A method for producing the splint of claim 1, comprising the following steps:
   cutting of multi-ply sheet so as to obtain a substantially rectangular shaped main band and a plurality of slits die cut to form a plurality of laces having the first end integrally joined to the sheet with the first end integrally joined to said main band;

application of at least one gripping element to the second end of said laces, the at least one gripping element being adapted to be fastened on the surface of the main band;

application a comb-shaped insert to said laces so that the laces enter respective gaps between the teeth in the comb-shaped insert; and securing of the fastening strip to said teeth of the comb-shaped insert, said fastening strip being adapted to be fastened on the upper surface of the main band.

3. The method according to claim 2, wherein said cutting step entails formation of long slits on at least one side strap of said main band, so as to form said laces.

4. The method according to claim 3, wherein said at least one gripping element is applied by sewing to an end of said at least one side strap.

5. The method according to claim 4, wherein said comb-shaped insert is applied by inserting the teeth into said long slits of the side strap.

6. The method according to claim 4, wherein said fastening strip is secured by sewing around said teeth of the comb-shaped insert.

7. The method according to claim 3, wherein said comb-shaped insert is applied by inserting the teeth into said long slits of the at least one side strap.

8. The method according to claim 7, wherein said fastening strip is secured by sewing around said teeth of the comb-shaped insert.

9. The method according to claim 3, wherein said comb-shaped insert is applied by inserting the teeth into said long slits of the side strap.

10. The method according to claim 3, wherein said fastening strip is secured by sewing around said teeth of the comb-shaped insert.

11. The method according to claim 2, wherein said fastening strip is secured by sewing around said teeth of the comb-shaped insert.

12. The splint according to claim 1, wherein the gaps between the teeth of said comb-shaped insert end in substantially C-shaped seats with a greater width than that of the laces to allow the laces to slide in said seats so as to adjust a position of the fastening strip.

13. The splint according to claim 1, wherein said laces are obtained by means of long slits formed in at least one side strap joined to said substantially rectangular main band, so that said teeth of the comb-shaped insert can be inserted in said long slits between the laces.

14. The splint according to claim 1, wherein said at least one gripping element are applied to an end of at least one side strap in which said laces are formed.

15. The splint according to claim 1, wherein said insert is made of plastic or Nylon.

16. The splint according to claim 1, wherein said fastening strip is joined to said teeth of the comb-shaped insert by sewing so as to surround said teeth.

17. The splint according to claim 1, wherein the splint further comprises pockets on said main band configured to receive stiffening plates.

18. A splint comprising:
a substantially rectangular main band, adapted to be closed in a tubular shape around a part of a body to be protected;
a plurality of slits die cut to form a plurality of laces each having a first end integrally joined to the splint with the first end integrally joined with one side of said substantially rectangular main band;
at least one gripping element connected to a second end of said laces and adapted to be fastened to an upper surface of the substantially rectangular main band, said at least one gripping element being able to be gripped by a user to tighten the laces and to close said substantially rectangular main band in a tubular configuration around the part of the body to be protected;
a comb-shaped insert provided with teeth spaced apart from each other so as to form gaps wherein said laces can be inserted;
a fastening strip joined to said teeth of the comb-shaped insert and adapted to be fastened onto the upper surface of the substantially rectangular main band; and
a central slit formed in said substantially rectangular main band to accommodate a thumb of a hand.

19. A splint comprising:
a substantially rectangular main band, adapted to be closed in a tubular shape around a part of a body to be protected;
a plurality of slits die cut to form a plurality of laces each having a first end integrally joined to the splint with the first end integrally joined with one side of said substantially rectangular main band;
at least one gripping element connected to a second end of said laces and adapted to be fastened to an upper surface of the substantially rectangular main band, said at least one gripping element being able to be gripped by a user to tighten the laces and to close said substantially rectangular main band in a tubular configuration around the part of the body to be protected;
a comb-shaped insert provided with teeth spaced apart from each other so as to form gaps wherein said laces can be inserted, said teeth having a tapered shape or an isosceles triangle shape; and
a fastening strip joined to said teeth of the comb-shaped insert and adapted to be fastened onto the upper surface of the substantially rectangular main band,
wherein said laces are obtained by means of long slits formed in at least one side strap joined to said substantially rectangular main band, so that said teeth of the comb-shaped insert can be inserted in said long slits between the laces.

* * * * *